(12) United States Patent
Vanhee

(10) Patent No.: US 6,232,617 B1
(45) Date of Patent: May 15, 2001

(54) APPARATUS FOR DETECTING SURFACE DEFECTS ON RUNNING METAL STRIP

(75) Inventor: Patrick Vanhee, Briey (FR)

(73) Assignee: Sollac, Puteaux (FR)

( * ) Notice: Subject to any disclaimer, the term of this patent is extended or adjusted under 35 U.S.C. 154(b) by 0 days.

(21) Appl. No.: 09/342,237

(22) Filed: Jun. 29, 1999

(30) Foreign Application Priority Data

Jul. 21, 1998 (FR) .................................................. 98 09272

(51) Int. Cl.[7] .................................................. G01N 21/88
(52) U.S. Cl. .................................. 250/559.45; 250/559.4
(58) Field of Search ........................... 250/559.45, 559.4, 250/559.46, 559.22, 559.42; 356/237.2, 237.4, 237.5, 239.7; 382/204, 266, 154

(56) References Cited

U.S. PATENT DOCUMENTS 5,568,313 * 10/1996 Steenblik et al. .

FOREIGN PATENT DOCUMENTS

| 0 731 350 A1 | 9/1996 | (EP) . |
| 58-204356 | 11/1983 | (JP) . |
| 60-179639 | 9/1985 | (JP) . |
| WO 98/01746 | 1/1998 | (WO) . |

* cited by examiner

Primary Examiner—Que T. Le
(74) Attorney, Agent, or Firm—Nixon Peabody LLP; Thomas W. Cole

(57) ABSTRACT

The invention relates to an apparatus for detecting surface defects on a running metal strip (1), which comprises means (2) for illuminating the area (3) of the strip (1) to be inspected, at least one pair of cameras (4, 5) each periodically capturing an image of the same portion (6) of said area (3), a computing unit (7) comprising means for reconstructing a stereoscopic image of said portion (6) from the images provided by the pair of cameras (4, 5), means for detecting, on said stereoscopic image, those objects which exhibit a relief—as a projection or as an indentation—with respect to the surface of the strip (1) greater than a predetermined threshold, means for analyzing the images of said objects and means (10) for displaying the result of this analysis to the operator.

1 Claim, 1 Drawing Sheet

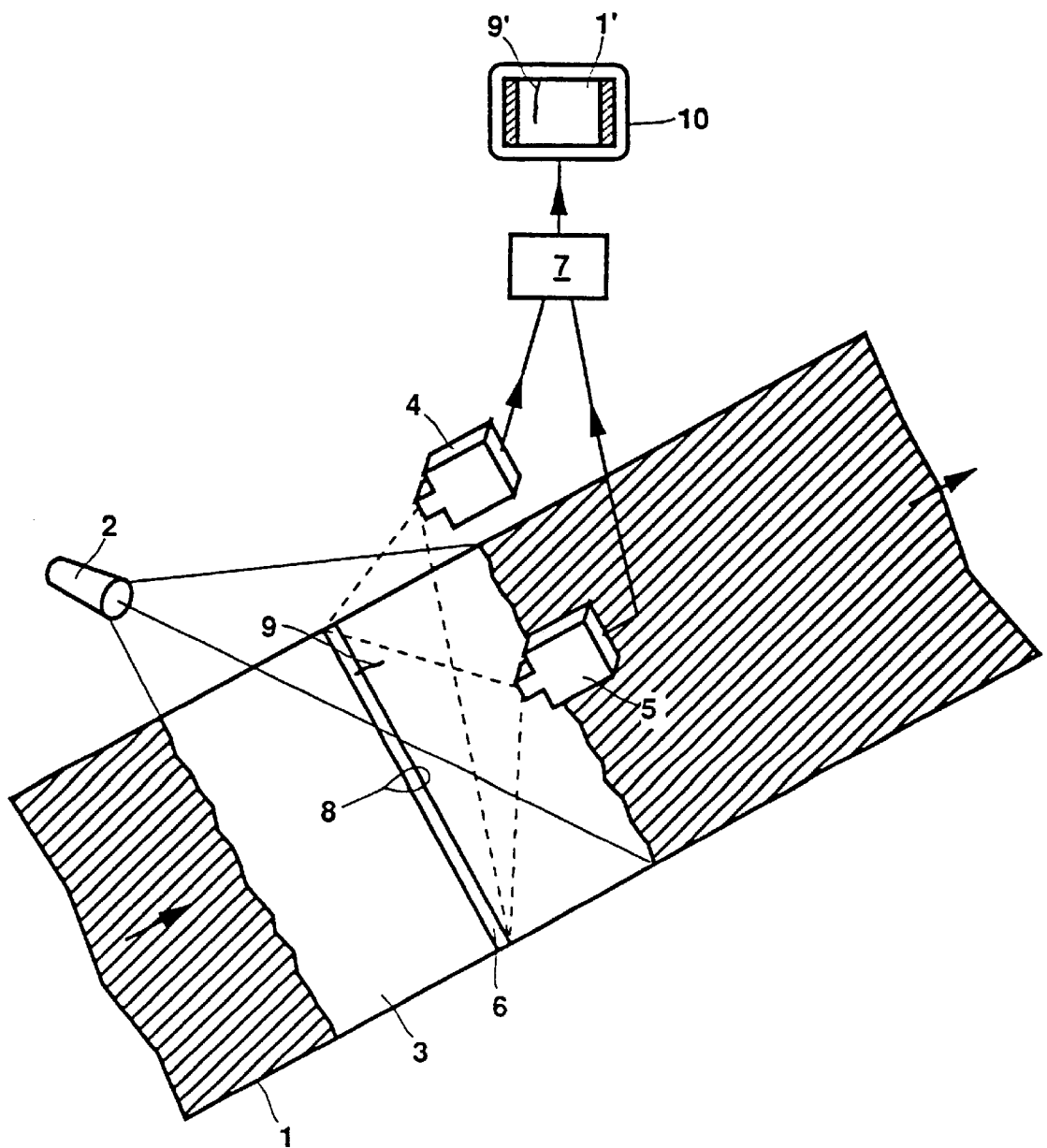
Single figure

APPARATUS FOR DETECTING SURFACE DEFECTS ON RUNNING METAL STRIP

FIELD OF THE INVENTION

The invcention relates to the production of metal strip, especially steel strip. More specifically, it relates to the techniques of checking the surface quality of such strip.

PRIOR ART

Plants for producing metal strip, especially steel strip, from initially thicker products comprise tools such as rolling mills, annealing furnaces and pickling plants. Before and/or after the product passes through these tools, it is common practice to inspect its surface using automatic apparatuses for the purpose of detecting thereon the possible presence of metallurgical defects such as depressions, scratches, blisters, remnants of scale, etc. The presence of such defects may indicate some malfunction of the equipment located upstream of the inspection, which have to be remedied, and may make it pointless to continue to process the product if the defects are serious enough to prevent final products of the desired quality being obtained.

Apparatuses for inspecting the surface of metal strip which are conventionally used essentially comprise:

- means for illuminating the area of the strip to be inspected;
- a linear or matrix camera which periodically captures an image of said area, at time intervals close enough together for complete inspection of the strip to be possible;
- a unit for processing this image, which extracts therefrom the "objects" which stand out by their color or their reflecting power from the uniform background which forms the surface of the strip and which makes it possible to recognize, from among these objects, those which actually constitute metallurgical defects and those which correspond to other phenomena which have no effect on the quality of the strip; this recognition takes place using software which compares the characteristics of the objects detected with those normally observed in the case of defects that the unit must indicate to the operator.

Among the objects detected by the image processing unit and that have to be recognized as not being metallurgical defects (and therefore not to be indicated as such to the operator), mention may be made of slightly whitish stains which remain on the surface of the strip after it has been pickled, or oil residues. Experience shows that a very high proportion (sometimes more than 90%) of the objects detected fall within this category. It follows that most of the computing time of the image processing unit is devoted to analyzing objects of no interest to the operator.

SUMMARY OF THE INVENTION

The object of the invention is to propose an apparatus for detecting surface defects on metal strip which allows this detection operation to be carried out more effectively than the apparatuses of the prior art.

For this purpose, the subject of the invention is an apparatus for detecting surface defects on a running metal strip, which comprises means for illuminating the area of the strip to be inspected, at least one pair of cameras each periodically capturing an image of the same portion of said area, a computing unit comprising means for reconstructing a stereoscopic image of said portion from the images provided by the pair of cameras, means for detecting, on said stereoscopic image, those objects which exhibit a relief—as a projection or as an indentation—with respect to the surface of the strip greater than a predetermined threshold, means for analyzing the images of said objects and means for displaying the result of this analysis to the operator.

As will have been understood, the invention consists in inspecting a given area of the strip by discriminating, from among the objects which are distinguished by the unit, those which exhibit a relief (as a projection or as an indentation) with respect to that surface portion of the strip which surrounds them and those which do not exhibit such a relief. It is established as a principle that the objects which do not exhibit relief (or in general a relief less than a predetermined threshold) are merely oily residues or stains and do not correspond to metallurgical defects. It is therefore pointless to continue to process their image. As regards objects exhibiting a relief, these are regarded as metallurgical defects and processed by the unit in the usual way, so as to determine their precise nature and their degree of seriousness, and to indicate them to the operator. This inspection is carried out no longer using a single camera, but two cameras aimed at the same area of the strip, according to the principle of stereoscopic vision.

The advantages of the apparatus according to the invention over apparatuses of the prior art can be exploited in two ways. It is possible to choose to keep the unit operating with its usual performance with regard to the detection of metallurgical defects, but this performance will be able to be achieved using less powerful (and therefore less expensive) computing means than previously since it will no longer be necessary to process the images of objects without relief, which are manifestly not metallurgical defects. It is also possible to choose to keep the computing means operating with their usual performance and to devote the computing power made available by the elimination from the processing of objects without relief to a finer detection, identification and display of the defects and/or to more rapid processing of their images. This rapid processing makes it possible to inspect a strip running at a higher speed than in the prior art and therefore makes it possible to accompany an increase in the productivity of the plant for manufacturing the strip.

BRIEF DESCRIPTION OF THE DRAWING

The invention will be more clearly understood on reading the description which follows, given with reference to the single appended FIGURE which shows diagrammatically an example of the apparatus according to the invention.

DESCRIPTION OF THE DRAWING

The single FIGURE shows a running steel strip 1, seen at any point in a plant for manufacturing such strip (for example, entering or leaving a cold-rolling mill or a pickling bath or an annealing furnace) in which it is desired to detect the presence of metallurgical defects. The apparatus for detecting these faults comprises, according to the invention, means 2 for illuminating an area 3 covering the entire width of the strip. Two cameras 4, 5 are pointed at the same portion 6 of this illuminated area 3, under conditions allowing a stereoscopic image of said portion 6 to be obtained by the superposition of the images periodically and simultaneously captured by each camera 4, 5. In practice, the optical axes of the cameras 4, 5 may be separated by approximately 10 to 20 cm. This stereoscopic image is reconstructed by a computing unit 7, using known methods since the principle of stereoscopic vision is already applied in apparatuses for the dimensional control of running metal strip, so as to take into account flatness defects in the strip. The processing unit 7 starts by digitizing the images captured by each camera 4, 5. It then extracts from each image those objects which have a color, texture or contour anomaly with respect to the uniform background which is normally formed by the illuminated surface 3 of the strip 1 in the viewed portion 6. The images of these objects, obtained by each of the cameras 4, 5, are then compared and the processing unit 7 analyses the dimensional and positional differences in the image planes of each object seen by each camera 4, 5, using the stereoscopic image that it has been able to reconstruct. If the object is a stain 8 or a thin layer of liquid, such as a rolling oil, it does not exhibit any significant relief with respect to the surface of the strip 1 and its two images should be identical. On the other hand, if the object is a metallurgical defect, such as a crack 9, a scratch, a mill scale or a depression, it should exhibit such a relief, as a projection or as an indentation depending on the type of defect, which results in different images captured by each camera 4, 5. Consequently, if this relief is zero or does not exceed a certain predetermined threshold, the processing unit regards the object examined as not a metallurgical defect, its processing is not continued and its existence is not indicated to the operator. However, if the relief exceeds said threshold, the processing of the image of the object continues in the usual way by comparing this image with reference characteristics representative of the various types of defects normally observed on running strip during its manufacture. This comparison results in a defect being identified and its dimensions determined, thereby allowing its seriousness to be estimated. Once the defect has been identified and analysed, it is indicated to the operator, for example by means of a display screen 10 which, in the figure, shows the image 1' of the strip 1 and the image 9' of the crack 9. On the other hand, the stain 8, which is not regarded as a metallurgical defect, does not appear on the screen 10.

Since, according to the invention, this operation of analyzing the apparent defect is only carried out on those detected objects which exhibit a relief with respect to the strip, i.e. a small proportion of the objects which are firstly detected, it is possible, if as powerful a processing unit 7 as in the prior art is retained, to install image processing software into it which is more complex and of higher performance. It is thus possible to achieve greater resolution in the detection and the analysis of the defects, and/or greater speed in carrying out this analysis, thereby making it possible to inspect strip running at a higher speed.

It is also conceivable to depart from the precise mode of data processing that has just been described, the essential point being, in order to remain within the scope of the invention, that, by virtue of the possibilities of stereoscopic vision provided by the pair of cameras 4, 5, a discrimination be made between those objects exhibiting a relief with respect to the surface of the strip from those which do not exhibit a relief, and that only the images of the objects in relief are subjected to powerful analysis.

In the example which has been described, only a single pair of cameras 4, 5, each pointing at the same area extending over the entire width of the strip 1, is used. However, it is also possible to use several pairs of cameras, each covering only part of the width of the strip 1.

It is quite obvious that the invention can be applied to the detection of surface defects on any running metal strip, and not only on steel strip.

What is claimed is:

1. An apparatus for detecting surface defects on a running metal strip (1), which comprises means (2) for illuminating the area (3) of the strip (1) to be inspected, at least one pair of cameras (4, 5) each periodically capturing an image of the same portion (6) of said area (3), a computing unit (7) comprising means for reconstructing a stereoscopic image of said portion (6) from the images provided by the pair of cameras (4, 5), means for detecting, on said stereoscopic image, those objects which exhibit a relief—as a projection or as an indentation—with respect to the surface of the strip (1) greater than a predetermined threshold, means for analyzing the images of said objects and means (10) for displaying the result of this analysis to the operator.

* * * * *